United States Patent
Fernandez Garcia et al.

(10) Patent No.: US 11,319,574 B2
(45) Date of Patent: May 3, 2022

(54) METHOD FOR THE RAPID DETERMINATION OF SUSCEPTIBILITY OR RESISTANCE OF BACTERIA TO ANTIBIOTICS

(71) Applicant: ABM Technologies, LLC, Navasota, TX (US)

(72) Inventors: Jose Luis Fernandez Garcia, Oleiros (ES); Jaime Gosalvez Berenguer, Colmenar Viejo (ES); Rebeca Santiso Brandariz, A Coruna (ES); Maria Tamayo Novas, A Coruna (ES); German Bou Arevalo, Culleredo (ES)

(73) Assignee: ABM Technologies, LLC, Navasota, TX (US)

( * ) Notice: Subject to any disclaimer, the term of this patent is extended or adjusted under 35 U.S.C. 154(b) by 289 days.

(21) Appl. No.: 14/322,626

(22) Filed: Jul. 2, 2014

(65) Prior Publication Data
US 2015/0010940 A1    Jan. 8, 2015

(30) Foreign Application Priority Data
Jul. 4, 2013   (EP) .................................... 13382271

(51) Int. Cl.
C12Q 1/18        (2006.01)
C12Q 1/04        (2006.01)

(52) U.S. Cl.
CPC ................. *C12Q 1/18* (2013.01); *C12Q 1/04* (2013.01); *G01N 2800/44* (2013.01)

(58) Field of Classification Search
CPC ......... C12Q 1/18; C12Q 1/04; G01N 2800/44
See application file for complete search history.

(56) References Cited

U.S. PATENT DOCUMENTS

| 2010/0129803 A1 | 5/2010 | Gosalvez Berenguer et al. |
| 2012/0045820 A1 | 2/2012 | Stroman |
| 2013/0008793 A1 | 1/2013 | Chung et al. |
| 2016/0102334 A1 | 4/2016 | Jung et al. |

FOREIGN PATENT DOCUMENTS

| CA | 2842865    | * | 1/2013  | ............... C12Q 1/18 |
| CA | 2842865 A1 |   | 11/2014 |                          |
| EP | 0135023 A2 |   | 3/1985  |                          |
| WO | 1992019763 A1 |   | 11/1992 |                     |
| WO | 9321511 A1 |   | 10/1993 |                          |
| WO | 9937799 A1 |   | 7/1999  |                          |
| WO | 2012021802 A2 |   | 2/2012 |                      |
| WO | WO2012021802 | * | 2/2012 | ............... C12Q 1/18 |
| WO | 2013014324 A1 |   | 1/2013 |                       |

OTHER PUBLICATIONS

Santiso et al. A rapid in situ procedure for determination of bacterial susceptibility or resistance to antibiotics that inhibit peptidoglycan biosynthesis. BMC Microbiology. 2011;11(191):1-14.*

Chung et al. Screening of Antibiotic Susceptibility to β-Lactam-Induced Elongation of Gram-Negative Bacteria Based on Dielectrophoresis. Anal. Chem. 2012;84:3347-3354.*
Ferraro MJ. Should we reevaluate antibiotic breakpoints? Clinical Infectious Diseases. 2001;33(Suppl 3):S227-9.*
Turnidge et al. Setting and revising antibacterial susceptibility breakpoints. Clinical Microbiology Reviews. 2007;391-408.*
International Search Report and Written Opinion for International Appl. No. PCT/US2014/045225 dated Nov. 28, 2014.
European Intent to Grant dated Aug. 23, 2016 in related EP Appl. No. 13382271.8.
New Zealand Examination Report dated Jan. 18, 2017 in related NZ Appl. No. 630583.
Chinese Examination Report dated Jan. 11, 2017 in related CN Appl. No. 201480037680.2.
EP Extended Search Report dated Nov. 18, 2013, issued in related EP Application No. 13382271.8 (4 pp).
Braga, P.C., et al., "Cefodizime: effects of sub-inhibitory concentrations on adhesiveness and bacterial morphology of *Staphylococcus aureus* and *Escherichia coli*: comparison with cefotaxime and ceftraixone", Jour. of antimocrobial Chemotherapy (1997)39, 79-84.
Chantratita, N., et al., "antimicrobial resistance to ceftazidime involving loss o penicillin-binding protein 3 in Burkholderia pseudomallei", (2011) PNAS vol. 108 No. 41, 17165-17170.
Curtis, N.A., et al., "Competition of beta-lactam antibiotics for the penicillin-binding proteins of Pseudomonas aeruginosa, Enterobacter cloacae, Klebsiella aerogenes, Proteus rettgeri and *Escherichia coli*: comparison with antibacterial activity and effects upon bacterial morphology", Antimicrobial Agents and Chemotherapy 16, No. 3 (1979): 325-328.
Hashimoto, H., et al., "Database Compendex: Measurement of Bacterial Size Distribuion Using Laser Light Scattering" On-line, Engineering Information, Inc., NY, (1984) 1 pp.
Hashimoto, H., et al., "Rapid Bacterial Testing Method by Size Distribution Measurement with Laser Light Scattering", IEICE Transactions (1976-1990) 68, No. 5 (1985): 304-308.
Ingham, C.J., et al., "Rapid antibiotic sensitivity testing and trimethoprim-mediated filamentation of clinical isolates of the Enterobacteriaceae assayed on a novel porous culture support", Journal of Medical Microbiology (2006) 55, 1511-1519.
Limbert, M., et al., "Cefodizime, An Aminothiazolylcephalosporin, I. In Vitro Activity", Journal of Antibbiotics, 37, No. 8 (1984): 892-900.
Nakao, M., et al., "Light and Electron Microscopy of the Morphological Response of *Escherichia Coli* and Serratia Marcescens to Cefmenoxime (CE-1365), A new Broad-Spectrum Cephalosporin", Journal of Antibbiotics, 34.8 (1981): 1046-1054.

(Continued)

*Primary Examiner* — Lynn Y Fan
(74) *Attorney, Agent, or Firm* — Ryan Christensen; Hashim Rahman (57) ABSTRACT

A method of rapidly evaluating the susceptibility of a strain of bacteria to a cell wall synthesis inhibiting antibiotic based on an assessment of cell enlargement in response to doses of the cell wall synthesis inhibiting antibiotic which are correlated to breakpoints of bacterial susceptibility.

15 Claims, 2 Drawing Sheets

(56) References Cited

OTHER PUBLICATIONS

Nathan, P., et al., "Identifification of two new cell division genes that affect a high-molecular-weight penicillin-binding protein in Caulobactercrescentus", Journal of Bacteriology 170, No. 5 (1988): 2319-2327.
Sass, P., et al., "Antibiotic acyldepsipeptides activate ClpP peptidase to degrade the cell division protein Ftsz", Proceedings of the National Academy of Sciences 108, No. 42 (2011): 17474-17479.
Wiegand, I., et al., "Effect of inoculum density on susceptibility of Plesiomonas shigelloides to cephalosporins", Journal of Antimicrobial Chemotherapy 54, No. 2 (2004): 418-423.
Baldoni D., et al., "Performance of microcalorimetry for early detection of methicillin resistance in clinical isolates of *Staphylococcus aureus*", J Clin Microbiol 2009; 47:774-776.
Hoettges K.F., et al., "Rapid determination of antibiotic resistance in *E. coli* using dielectrophoresis", Phys Med Biol 2007;52:6001-6009.
Rolain J.M., et al., "Real-time PCR for universal antibiotic susceptibility testing", J Antimicrob Chemother 2004;54:538-541.
Santiso R., et al., "Rapid and simple determination of ciprofloxacin resistance in clinical strains of *Escherichia coli*", J Clin Microbiol 2009;47: 2593-2595.
Santiso R., et al., "A rapid in situ procedure for determination of bacterial susceptibility or resistance to antibiotics that inhibit peptidoglycan biosynthesis", BMC Microbiol 2011;11:191, 15 pp.
Bauer, A. W., et al., "Antibiotic Susceptibility Testing by a Standardized Single Disc Method", Am Jour Clin Pathol 1966; 45:4 (493-496).
Argentinian Office Action dated Aug. 31, 2017 in related AR Appl. No. P20140102482.
Lorian, V. et al., "Weight and morphology of bacteria exposed to antibiotics" The Influence of Antibiotics on the Host-Parasite Relationship II, 1985. pp. 65-66.
Lorian, Victor et al., "Minimal Antibiotic Concentrations of Aminoglycosides and ,B-Lactam Antibiotics for Some Gram-Negative Bacilli and Gram-Positive Cocci" The Journal of Infectious Diseases, vol. 139, No. 5, May 1979. pp. 599-603.
Tanaka, Mayumi et al., "In Vitro and In Vivo Activities of DQ-2556 and Its Mode of Action" Antimicrobial Agents and Chemotherapy, Dec. 1992. pp. 2595-2601.
Decoster, A, "Classification Des Antibiotiques" Antibiotiques, 2012.
Cushnie, Tim et al., "Morphological and ultrastructural changes in bacterial cells as an indicator of antibacterial mechanism of action" Cell. Mol. Life Sci., 2016. pp. 1-28.
Choi, J et al., "Single-Cell Morphological Analysis for Rapid Antimicrobial Susceptibility Test" Transducers, 2015. pp. 730-734.
Otero, Fatima et al., "Rapid Detection of Antibiotic Resistance in Gram-Negative Bacteria Through Assessment of Changes in Cellular Morphology" Microbial drug resistance, vol. 23, No. 2, 2017. pp. 157-162.
Kjeldsen, Thea et al., "Extended spectrum Beta-lactamase-producing *Escherichia coli* forms filaments as an initial response to cefotaxime treatment" BMC Microbiology, 2015. pp. 2-6.
Brody's human pharmacology, "Bacterial Cell Wall Synthesis Inhibitors—Brody's Human Pharmacology: With Student Consult", [cite Jul. 9, 2017] disponible sur :[http://doctorlib.info/pharmacology/pharmacology/48.html].
Fredborg, Marlene et al., "Automated image analysis for quantification of filamentous bacteria" BMC Microbiology, 2015. pp. 1-8.
Zhanel, George et al., "Subinhibitory antimicrobial concenlrations review of in vitro and in vivo data" Can J Infect Dis, vol. 3, No. 4, Jul. 1992. pp. 193-201.
Chung, Cheng-Che et al., "Screening of Antibiotic Susceptibility to A-Lactam-Induced Elongation of Gram-Negative Bacteria Based on Dielectrophoresis" Analytical chemistry, vol. 84, Dec. 2012. pp. 3347-3354.
Leboffe, Michael et al., "A photographic atlas for the microbiology laboratory 4th edition" USA: Morton Publishing, 2011.
Van Boven, CPA et al. "Size determination by the filtration method of the reproductive elements of group A *Streptococcal* L Forms" J Gen Microbiol, vol. 52, 1968. pp. 403-412.
Chau, Frangoise et al., "Flow cytometry as a tool to determine the effects of cell wall active antibiotics on vancomycin susceptible and resistant Enterecoccus faecalis strains" Antimicrobial Agents and Chemotherapy, 2011. pp. 395-398.
Nuding, Sabine et al., "Detection, identification and susceptibility testing of bacteria by flow cytometry" Bacteriology & Parasitology, 2013. pp. 1-9.
Lacoste, Judith, "Transmitted light contrasting techniques : BF,DF,PC, pol,DIC" McGill systems biology program, 2010.
EP Notice of Opposition issued on Nov. 22, 2017 in related EP Application No. 13382271.8.
Chinese Office Action dated Mar. 28, 2018 issued in related CN Appl. No. 201480037680.2.
Canadian Office Action dated Jul. 22, 2019 issued in related CA Appl. No. 2914708.

\* cited by examiner

METHOD FOR THE RAPID DETERMINATION OF SUSCEPTIBILITY OR RESISTANCE OF BACTERIA TO ANTIBIOTICS

This application claims priority under 35 U.S.C. § 119 to European patent application EP 13382271.8, filed Jul. 4, 2013, the disclosure of which is incorporated herein by reference.

FIELD OF THE INVENTION

The present invention relates broadly to the field of biotechnology, and more particularly to microbiology pertaining to human health, veterinary health and environmental health. Certain embodiments described relate to methods for the rapid determination of the susceptibility or resistance of cultured bacteria to antibiotics.

BACKGROUND OF THE INVENTION

The European Center for Disease Control (ECDC) reports 25,000 annual deaths due to multi-resistant pathogens, i.e. pathogens resistant to several antibiotics. Well-selected, early antibiotic treatments provide the best defense against such multi-resistant pathogens. Given the high prevalence of resistances, current procedures require a bacterial culture for identification of the microorganism followed by an antibiogram, which routinely requires 2-3 days of bacterial growth. The step of culturing bacteria to construct an antibiogram alone generally requires about one day of incubation, or about a minimum of 18 hours. Therefore, a need exists for rapidly determining an antibiotic treatment so that an effective treatment can be administered quickly.

Once cultured, conventional methodologies evaluate resistance of bacteria to an antibiotic by a comparison against an established Minimum Inhibitory Concentration (MIC). The Minimum Inhibitory Concentration (MIC) is generally regarded as the lowest dose of antibiotic that significantly inhibits bacterial growth as determined by the standard techniques of microdilution or by an E-test. International organizations like the Clinical and Laboratory Standards Institute (CLSI), establish the concentrations of each specific antibiotic which are generally used as references of susceptibility, intermediate resistance and resistant for each specific bacterium. For example, a strain of *Acinetobacter baumannii* is considered susceptible to imipenem when its MIC is ≤4 µg/ml, intermediate when the MIC is between 4 µg/ml and 8 µg/ml, and resistant when the MIC is ≥16 µg/ml.

A great concern exists globally due to the progressive increase of critical nosocomial (hospital acquired) infectious diseases, often in immunocompromised patients and frequently from the Intensive Care Unit (ICU). For a variety of reasons, such infections may be associated with a high mortality rate. The pathogens may infect a patient through intrusive, but necessary, medical means, such as in the respiratory pathway during mechanical ventilation, in the urinary tract or blood vessels via catheters or even through skin wounds such as incisions required for any number of medical procedures. Many pathogens associated with these problems belong to the gram-negative bacilli family. For example, frequently *Acinetobacter baumannii, Klebsiella pneumoniae, Pseudomonas aeruginosa* and some enterobacteria, are resistant to several antibiotics. Given the relative long time necessary to perform the standard antibiogram, antibiotics are usually empirically provided. This treatment may be ineffective in 20-40% of cases, and a change of antibiotics later may have a reduced probability of success. In these urgent scenarios with increased risk of death or severe complications, a rapid system to determine an effective antibiotic treatment is of great interest. Therefore, a need exists for the rapid determination of bacterial susceptibility to antibiotics in standardized dosages, which may save lives and reduce health care costs.

The first line of defense in combating infectious diseases often relies on antibiotics generally known to be effective based on the likely pathogen involved. However, antibiotic misuse or overuse may lead to increasingly resistant strains of bacteria. In order to prevent misuse, practitioners may attempt to isolate bacteria from blood samples or samples of other fluid for in vitro testing, such as an antibiogram, concurrently with the initial antibiotics.

An antibiogram results from clinically testing an isolated strain of bacteria in vitro for its susceptibility to antibiotics. A common methodology for constructing an antibiogram based on diffusion is the Kirby-Bauer method (Bauer A W, Kirby W M M, Sherris J C, Turck M. *Antibiotic susceptibility testing by a standardized single disc method. Am J Clin Pathol* 1966; 45:493-496). In the semi quantitative Kirby-Bauer method, several discs containing different antibiotics are placed in different zones of nutrient rich bacteria culture. Because the antibiotic diffuses into the agar away from the disc, the diameter around the disc in which bacteria does not grow is suggestive of the minimum inhibitory concentration (MIC) of that antibiotic to the cultured strain of bacteria. A quantitative method may rely on a series of vials having progressively lower concentrations of the antibiotic in question. The vial with the lowest concentration of antibiotic in which the bacteria cannot grow provides the minimum inhibitory concentration of that antibiotic to the tested strain of bacteria.

Each of the diffusion and the dilution methods rely on the principal of inhibiting bacterial proliferation in a nutrient rich medium and this requires sufficient time for many reproductive cycles of bacteria. As such, both methodologies may require a minimum of between 18 hours and 24 hours.

Previous attempts to improve the speed of evaluating bacterial susceptibility to antibiotics have failed to provide the significant reduction in time required to meet the above described needs. WO/1992/019763 describes a previous method incorporating a nutrient-containing fluorogenic compound having a fluorescent reporter. A microorganism which continues to grow in the presence of an antibiotic metabolizes the compound releasing the fluorescent reporter, whereas the metabolic processes of susceptible strains release fewer fluorescent reporters. This methodology still requires sufficient incubation time allowing the release of a sufficient number of fluorescent reporters and it may take around eight hours to obtain results.

The above described methodologies are based on the evaluation of the microbial growth. Results from such assays can be accelerated using a time-lapse microscopy or real-time microscopy approach. Software may be employed to facilitate the interpretation of these results. Commercialized systems like the MicroScan WalkAway, Vitek, and Wider may be capable of determining susceptibility or resistance to antibiotics from a specific microorganism in around 6-9 hours.

Another approach for assessing the response of a bacterial strain to an antibiotic is the sequential evaluation of the increase of specific bacterial DNA sequences, which is directly related to the number of bacteria, using a real-time quantitative polymerase chain reaction assay (q-PCR). Results of possible affectation of bacterial growth by the antibiotic could be obtained after 6 hours of culture (Rolain J M, Mallet M N, Fournier P E, Raoult D. *Real-time PCR for universal antibiotic susceptibility testing. J Antimicrob Chemother* 2004; 54:538-541).

Another experimental approach may be characterized as a dielectrophoresis system which detects changes in the electrophysiology of the cell after administration of the antibiotic (Hoettges K F, Dale J W, Hughes M P. *Rapid determination of antibiotic resistance in E. coli using dielectrophoresis. Phys Med Biol* 2007; 52:6001-6009). Other possibility is the measure of the heat released by the bacterial culture, using microcalorimetry systems (Baldoni D, Hermann H, Frei R, Trampuz A, Steinhuber A. *Performance of microcalorimetry for early detection of methicillin resistance in clinical isolates of Staphylococcus aureus. J Clin Microbiol* 2009; 47:774-776).

In the case of antibiotics that act at the cell wall level, like the β-lactams, European Patent EP0135023 describes specific substrates for detecting the activity of cytoplasmic proteins or enzymes released to the medium when an antibiotic was effective. Another possibility is the evaluation of DNA fragments liberated to the medium (Santiso R, Tamayo M, Gosálvez J, Bou G, Fernández M C, Fernández J L. *A rapid in situ procedure for determination of bacterial susceptibility or resistance to antibiotics that inhibit peptidoglycan biosynthesis. BMC Microbiol* 2011; 11:19). The bacteria are enclosed in an agarose microgel on a slide and incubated with a lysing solution that only affects those cells whose cell wall has been affected and/or debilitated by the antibiotic. Only these bacteria release the nucleoid, which is visualized under fluorescence microscopy after DNA staining with a high-sensitivity fluorochrome. The bacteria resistant to the antibiotic are not affected by the lysing solution and do not release the nucleoid, thus keeping their standard shape. This procedure can be also adapted for the determination of the susceptibility or resistance to antibiotics that induce the fragmentation of the bacterial DNA, like the quinolones. To this purpose, the lysing solution must be stronger, so that all the bacteria release the nucleoids in a detectable manner. Those bacteria susceptible to the quinolone show fragmented DNA, i.e. diffused DNA fragments, whereas those resistant reveal intact nucleoids (Santiso R, Tamayo M, Fernández J L, Fernández M C, Molina F, Gosálvez J, Bou G. *Rapid and simple determination of ciprofloxacin resistance in clinical strains of Escherichia coli. J Clin Microbiol* 2009; 47: 2593-2595). However, this methodology may occasionally result in false positive identification of a susceptible strain, which may consequently lead to ineffective antibiotic treatments. For example, some strains of *P. aeruginosa* which are categorized as intermediate or resistant to carbapenems, following the CLSI criteria, can release the nucleoid by affectation of the cell wall, so they may be misidentified as susceptible.

Each experimental approach has failed to provide a rapid and accurate measurement of bacterial susceptibility to standardized dosages of antibiotics, and the field generally continues to rely on the dilution and diffusion methods of constructing an antibiogram.

SUMMARY OF THE INVENTION

Certain embodiments of the claimed invention are summarized below. These embodiments are not intended to limit the scope of the claimed invention, but rather serve as brief descriptions of possible forms of the invention. The invention may encompass a variety of forms that differ from these summaries.

Some embodiments relate to a method of rapidly evaluating the susceptibility of an isolated strain of bacteria to a cell wall synthesis inhibiting antibiotic. The method may begin by establishing a bacteria culture of an isolated strain of bacteria and by combining one or more doses of a cell wall synthesis inhibiting antibiotic to different portions of the bacteria culture. The concentration of each of the one or more doses may be correlated to thresholds of antibiotic resistance for the isolated bacteria to the cell wall synthesis inhibiting antibiotic. The bacteria culture and the one or more antibiotic doses may then be incubated. After incubation, the cell length or cell size of the incubated bacteria may be assessed for each of the one or more cell wall synthesis inhibiting antibiotic doses. The susceptibility of the isolated bacteria to the cell wall synthesis inhibiting antibiotic may be classified based on the cell lengths or cell sizes of bacteria associated with each dose of the one or more doses of cell wall synthesis inhibiting antibiotic.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

MODES FOR CARRYING OUT THE INVENTION

As used throughout this description, the term "growth," when used in conjunction with bacteria, bacterial, microorganism and the like, should be understood as an increase in a number of cells, such as the proliferation of bacteria in a culture.

Similarly, terms such as "growth inhibition" should be understood as referring to inhibiting an increase in a numbers of cells, such as inhibiting bacterial proliferation in a bacteria culture.

As used throughout this description and claims, the term "enlargement," when used in conjunction with microorganism, bacteria, and the like, should be understood as an increase in the length and/or size of individual microorganisms, bacteria, and the like.

Embodiments of the present invention have demonstrated that the activity of certain antibiotics, and particularly antibiotics which inhibit cell wall synthesis or which inhibit peptidoglycan synthesis in different bacteria, can be reliably determined through the assessment of enlargement of cell size or length. To distinguish susceptible strains from intermediate or resistant strains, the bacteria may be incubated with doses of antibiotics which are much lower than those employed as breakpoints of susceptible, intermediate or resistant, established by the international organizations like the Clinical and Laboratory Standards Institute (CLSI) for the standard antibiograms based on evaluation of bacterial growth through microdilution or E-test. The concentrations of antibiotics established by the CLSI are adequate to discriminate susceptibility or resistance based on the cell lytic effect and cell growth inhibition.

The breakpoint concentrations of various cell wall synthesis inhibiting antibiotics indicated by the CLSI are higher than those concentrations which result in enlargement. Cellular enlargement by the activity of cell wall synthesis inhibiting antibiotics can be observed when incubating with the concentrations established by the CLSI for susceptibility, even in resistant strains of bacteria. Surprisingly, the instant invention provides evidence that it is possible to establish a correlation between the CLSI breakpoint concentrations for bacterial susceptibility and new breakpoint concentrations based on the presence or absence of cell enlargement in response to a cell wall synthesis inhibiting antibiotic. While various antibiotics have been known to have effects on the bacterial cell length, bacterial cell enlargement has never been considered as a parameter for determining the susceptibility/resistance of bacteria to these antibiotics. To this end, it is necessary to identify the minimum concentration of the antibiotic above which the bacterial cell size or length enlargement begins to be significant in a specific strain from a specific species of bacteria.

The minimum concentrations of antibiotics that discriminate susceptible, intermediate and resistant strains (or even just susceptible and resistant strains) to various cell wall synthesis inhibiting antibiotics can be empirically correlated for each species of microorganism to various antibiotics. As one example, several concentrations of antibiotic may be incubated with a large number of bacteria strains which have each been determined to be susceptible by MIC-CLSI testing. MIC-CLSI testing may incorporate traditional antibiogram methodologies such as growth/no growth obtained by diffusion, microdilution and/or an E-test. The minimum concentration of antibiotic which results in the enlargement of strains of bacteria identified as susceptible according to MIC-CLSI testing may be considered as a concentration correlated to the MIC-CLSI value for susceptible strains. Naturally, higher doses of antibiotics, such as doses correlated as breakpoints of intermediate resistance and of resistant, will also demonstrate cell enlargement. Alternatively, a susceptibility breakpoint may be correlated to other standardized susceptibility determinations, or even an independent determination of susceptibility.

For those bacteria which have MIC-CLSI values indicating intermediate strains, several concentrations of an antibiotic may be incubated with a large number of bacteria strains which have each been determined to be intermediately resistant by MIC-CLSI testing. The minimum concentration of antibiotic which results in the enlargement of those strains of bacteria may be considered as a concentration correlated to the MIC-CLSI threshold for intermediate resistance. Naturally, higher doses, such as a dose correlated to the breakpoint of resistance, will also result in cell enlargement. Alternatively, an intermediated breakpoint may be correlated to other standardized determinations of intermediate resistance, or even an independent determination of intermediate resistance.

Finally, several concentrations of antibiotic may be incubated with a large number of bacteria strains which have each been determined to be resistant by MIC-CLSI testing. The minimum concentration of antibiotic which results in the enlargement of those strains of bacteria may be considered as a concentration correlated to the MIC-CLSI value for resistant strains. Doses at or above the concentration correlated to the breakpoint of resistant strains may or may not result in cell enlargement, depending on the particular level of resistance of a particular strain. Alternatively, a resistant breakpoint may be correlated to other standardized determinations of resistant bacteria, or even an independent determination of resistant bacteria.

The described methods may be incorporated for testing various antibiotics which result in bacteria enlargement and may be particularly beneficial in testing cell wall synthesis inhibiting antibiotics. A bacterial cell wall is built on a scaffold which may be composed of the peptidoglycan or murein. This is a linear chain constituted by alternant N-acetylglucosamine (NAG) and N-acetylmuramic acid (NAM). A tetrapeptide is attached to NAM forms an interpeptidic bond with the tetrapeptide of the closest chain, stabilizing and strengthening the cell wall.

The main family of antibiotics that inhibit cell wall synthesis corresponds to the 3-lactams. These bactericidal agents interfere with the formation of the interpeptidic bonds through irreversible reactions that inhibit Penicillin Binding Proteins (PBPs), serine proteases or transpeptidases. Cephalosporins are a specific subfamily of $\beta$-lactams, comprising more than 60 antibiotics, grouped in five "generations", although the number of generations is under discussion. Cephalosporins, like ceftazidime, bind to several PBPs, although sometimes showing an affinity for specific ones, like PBP3. This action may result in cell enlargement or filamentation of bacteria by inhibiting the development of the intercellular septum, which is necessary for cell division.

Carbapenems are another $\beta$-lactam, which, unlike penicillins and cephalosporins, show a carbon atom in position 1 of the $\beta$-lactam ring, instead of sulphur. Imipenem, meropenem, ertapenem, faropenem, doripenem, panipenem, and panipenem/betamipron are common carbapemens. It should be appreciated that other antibiotics are also contemplated for use with certain embodiments of the claimed invention. For example, other antibiotics which inhibit cell wall synthesis are expected to provide similar correlations to CLSI breakpoints. In particular, those antibiotics which act to inhibit the production of peptidoglycan are expected to work in a similar manner.

Figure 1:
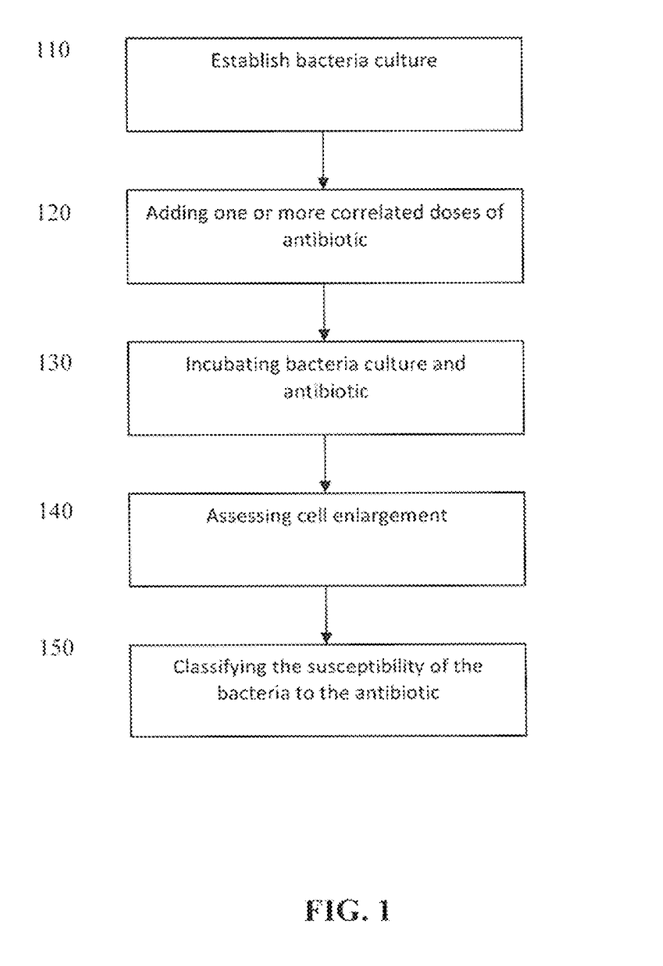
FIG. 1 illustrates a flow diagram of a method in accordance with certain embodiments described herein.

FIG. 1 illustrates a flow chart of a method in accordance with the certain embodiments of the invention. The method may begin at 110 with the step of establishing a bacteria culture from an isolated strain of bacteria. Bacteria may be collected from bodily fluids of a patient or animal for in vitro culturing by known techniques and protocols. The bacteria culture may be formed in a liquid broth, as well as, in a nutrient rich agar or even a minimal agar. In one embodiment, the bacteria may be formed into a pure culture demonstrating exponential growth. In the event the bacteria culture is not growing exponentially, the culture may be placed in a nutrient rich liquid, such as a culture broth, and incubated for an hour and a half prior to further steps. Bacteria collected for rapid detection may be any bacteria causing infection in a patient, or presented in the tissue or bodily fluids of a patient. While not limiting on the claimed invention, infections which may be problematic and which may benefit well from the foregoing methodology may present gram negative bacilli. As further non-limiting examples, the bacteria may be *Acinetobacter baumannii, Klebsiella pneumonia, Pseudomonas aeruginosa*, or another species in the enterobacteria family.

At step 120, the bacteria culture may be combined with one or more doses of an antibiotic. The antibiotic may comprise a cell wall synthesis inhibiting antibiotic, such as a $\beta$-lactam (Beta-lactam) or a glycopeptide. In a further non-limiting embodiment the antibiotic may be selected from a cephalosphorin or carbapenem. In one embodiment, concentrations for each dose of antibiotics may be established prior to deployment of this method from an empirical evaluation of multiple strains of the bacterium including a wide range of MICs, including susceptible, intermediate and resistant strains according to the CLSI, or from another competent body which promulgates similar definitions, such as the European Committee on Antimicrobial Susceptibility Testing (EUCAST) or The British Society for Antimicrobial Chemotherapy (B SAC). For example, a minimum concentration of the antibiotic may be empirically established which induces cell enlargement only in those strains of bacteria classified as susceptible according to the MIC-CLSI standards. This concentration may be considered correlated to the MIC-CLSI standard for a susceptible strain of bacteria. In one embodiment, this concentration correlated to the classification of a susceptible strain may be the only concentration of that antibiotic employed for a rapid determination of whether a strain of bacteria is susceptible or not-susceptible to a particular antibiotic. Such an embodiment may rapidly provide fundamental information a clinician urgently needs. Alternatively, multiple doses may be employed at concentrations that are correlated to minimum concentrations for differentiating susceptible, intermediate, and resistant strains of bacteria. In yet another embodiment antibiotic dosages are provided such that at least one provided which would significantly inhibit bacterial growth of susceptible bacteria strains and at least a second dosage is provided which would significantly inhibit bacterial growth of susceptible or intermediate bacteria, but not resistant bacteria.

The step of combining one or more doses may include introducing one or more concentrations of the antibiotic to separate physical locations on a plate, such as a Petri dish, or other flat culturing surface. The step of combining one or more doses may also include introducing doses into separate containers, such as test tubes having a culture broth.

Various method steps and examples may be described in terms of a single antibiotic and a single bacteria strain, but it should be appreciated multiple antibiotics may be tested at once in accordance with the claimed invention. For example, the one or more doses may comprise a single predetermined concentration from multiple antibiotics, or may comprise multiple concentrations from a variety of different antibiotics.

Once combined, the antibiotic and the bacteria culture may be incubated at step 130. After an hour of incubation with the antibiotic, bacteria may be assessed for enlargement in terms of cell length or cell size at step 140. Cell length and/or cell size may be assessed based on relative differences, such as compared against a control dose (i.e. antibiotic concentration of 0 µg/ml) or even compared to measurements taken prior to incubation with the antibiotic. The assessment may also be based on quantitative measurements. Assessment of cell enlargement may be made by every possible system of microscopy, such as bright field, dark field, phase contrast, interferential contrast, fluorescence, etc. In one embodiment, software may be employed which is capable of determining cell length or cell size and which may further include instructions for classifying the susceptibility based on quantitative measurements or relative comparisons. Such an assessment may also be made with various systems of cytometry, like flow cytometry or by filtering through membranes of different pore sizes or by any other methodology that discriminates cell sizes. In one embodiment, various existing kits may be modified. For example, bacteria may be suspended in a microgel on a slide and incubated in increasing alcohol baths, dried and examined under microscopy. Fluorescence microscopy after staining the bacteria enclosed in dried microgels, with a fluorochrome, like SYBR Gold, provides the advantage of obtaining perfect sharp images, without background, with great quality to accurately and confidently establish the cell size or length. The adaptation of the microgel procedure allows an integrated technological system, presented as a kit that complements those existing for a rapid determination of susceptibility or resistance to antibiotics that act at the cell wall.

Figure 2:
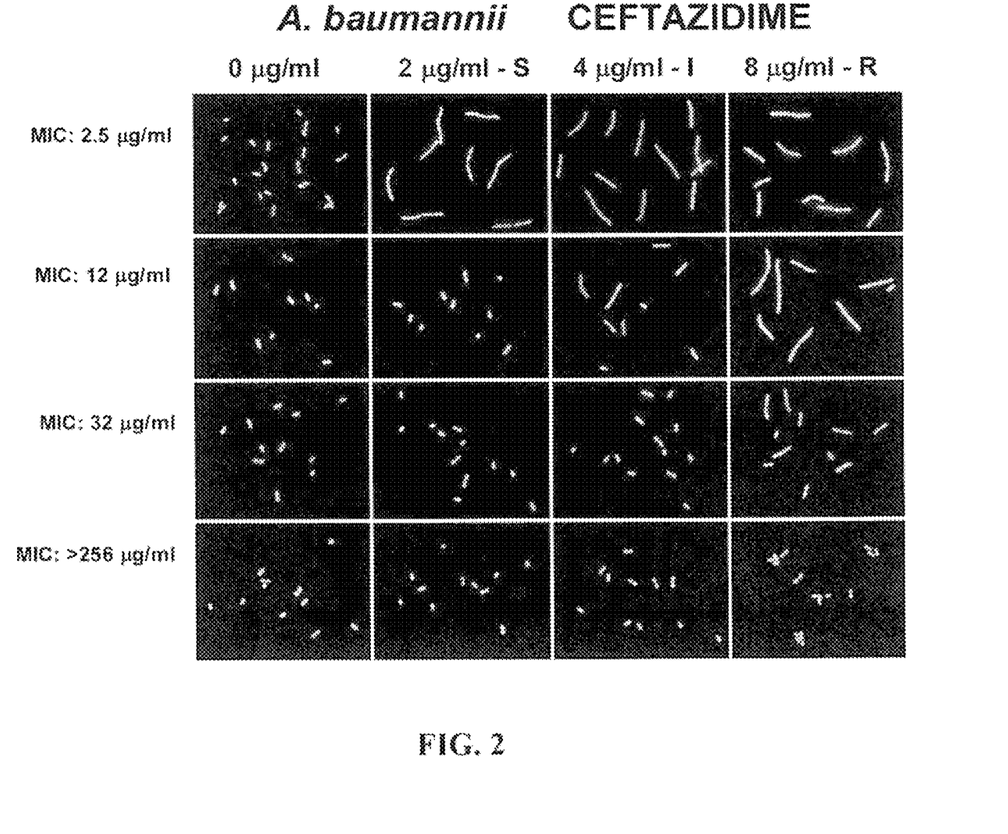
FIG. 2 illustrates images of *A. baumannii* strains incubated with antibiotics in accordance with certain embodiments described herein.

Once the cell length or cell enlargement is assessed, whether by relative comparison or by quantitative measurements, the strain of bacteria may be classified. As one example, the bacteria may be classified as susceptible, intermediate, or resistant, in accordance with the definitions provided by the CLSI. With reference to FIG. 2, classifications may quickly be made based upon the assessment of enlargement in response to the one or more doses of the antibiotic. However, other definitions may also be employed from other agencies. Dose concentrations may be empirically correlated by the same methodology previously described. As another example, the MIC breakpoint concentrations of the antibiotic established by the CLSI or other regulatory organizations may be periodically revised and could be changed. In this case, the breakpoint concentrations for the criterion of enlargement/no enlargement should be correlated with the new MIC breakpoints. For example, the methodology previously described may be utilized to correlate test dosages to susceptibility breakpoints, such as susceptibility breakpoints described in: *Performance standards for antimicrobial susceptibility testing: twenty-third informational supplement*. Clinical and Laboratory Standards Institute, Vol 33 No. 1. CLSI document M100-S23, January 2013, the contents of which are incorporated herein by reference. Similarly, test dosages may be correlated to susceptibility break points defined by other organizations, such as the European Committee on Antimicrobial Susceptibility Testing (EUCAST). Regardless of the susceptibility breakpoints utilized, a much faster determination of the same information is achieved through the steps described.

Steps 110 to 150 may be performed within an hour and a half, including an hour for incubation with the antibiotic and about 15 minutes of preparation of the microgel, dehydration with alcohols, drying, staining for the determination of cell enlargement. However, in the event the bacterial culture is not exponentially growing, an extra hour and a half of incubation in a liquid broth may be required to establish exponential growth.

Example 1

Concentrations of the cephalosporin antibiotic ceftazidime were correlated to the breakpoints for the classification of susceptible, intermediate and resistant strains of *Acinetobacter baumannii* according to the CLSI criteria. FIG. 2 shows images of various *A. baumannii* strains, including one susceptible strain, one intermediate strain and two strains resistant to the ceftazidime, according to the MIC-CLSI criteria. Several strains of *A. baumannii*, were incubated with ceftazidime for one hour, then enclosed in a microgel on a slide, dehydrated, stained with SYBR Gold and observed under fluorescence microscopy.

The first row of FIG. 2 illustrates images of a susceptible strain of *A. baumannii*, (having a MIC of 2.5 µg/ml) exposed to a control having no antibiotic, a second concentration of 2 µg/ml ceftazidime, a third concentration 4 µg/ml ceftazidime, and a fourth concentration of 8 µg/ml ceftazidime. The second row of FIG. 1 illustrates images of an intermediate strain of *A. baumannii* (having a MIC of 12 µg/ml) exposed to the same concentrations of ceftazidime. The third row illustrates images of a resistant strain of *A. baumannii* (having a MIC of 2.5 µg/ml) exposed to the same concentrations of ceftazidime and the fourth row illustrates a highly resistant strain. According to the CLSI criteria, a strain of *A. baumannii* is classified as susceptible when their MIC≤8 µg/ml; intermediate when 8 µg/ml≥MIC≤16 µg/ml; and resistant when MIC≥32 µg/ml.

New breakpoint concentrations of ceftazidime were ascertained from an inspection of the slides illustrated in FIG. 2. For example, the susceptible strain illustrated on the top row demonstrated enlargement from concentrations 2 µg/ml and up. The MIC determined by E-test for the susceptible strain was 2.5 µg/ml. The intermediate strain illustrated on the second row demonstrated enlargement beginning at concentrations of 8 µg/ml and up. The MIC determined by E-test for the intermediate strain was 12 µg/ml. The resistant strain illustrated on the third row demonstrated enlargement from concentrations 8 µg/ml and up. The MIC determined by E-test for the susceptible strain was 32 µg/ml. The highly resistant strain illustrated on the fourth row did not demonstrate enlargement at any tested concentration. The MIC determined by E-test for the highly resistant strain was greater than 256 µg/ml.

In summary, the breakpoint concentrations of ceftazidime following the criterion of cell enlargement (antibiotic concentrations, above the columns) are 4-times lower than those indicated by the CLSI for MICs. According to the CLSI, breakpoint MICs were ≤8-16-≥32 µg/ml (susceptible-intermediate-resistant), which are empirically coordinated to concentrations of ≤2-4-≥8 µg/ml in the case of cell enlargement. With the empirically correlated values cell enlargement/non-enlargement criterion susceptible and non-susceptible stains of bacteria can be determined with incubation in 2 µg/ml of antibiotic, instead of 8 µg/ml required by the former CLSI. More importantly, the incubation time required to make an enlargement/non-enlargement determination is drastically reduced as compared to previous methodologies.

Example 2

To validate the correlated breakpoint concentrations established in Example 1, 320 *A. baumannii* strains were processed. 51 of those strains were determined to be susceptible to ceftazidime according to MIC-CLSI established by an E-test, 35 strains were determined to be intermediate and 234 strains were determined to be resistant.

Each of the 320 strains of *Acinetobacter baumannii* were incubated with ceftazidime for an hour. Each dose was correlated to susceptibility breakpoints established in Example 1. The incubated samples were then assessed under microscopy for enlargement. The criterion of enlargement/non-enlargement was determined by a comparison to a control dose of 0 µg/ml. Strains were considered to be susceptible when they demonstrated enlargement in response to concentrations 2 µg/ml and up. Strains were considered to be intermediate when they demonstrated enlargement in response to concentrations 4 µg/ml and up. Strains were considered to be resistant when they demonstrated enlargement in response only to the 8 µg/ml dose, or not at any concentration. Using the criterion of enlargement/non-enlargement and the correlated breakpoint concentrations, each of the 320 strains were correctly identified.

Example 3

*Klebsiella pneumoniae*, another significant pathogen in clinical settings, was also evaluated. According to the CLSI criteria a strain of *K. pneumoniae* is classified as susceptible to ceftazidime when the MIC≤4 µg/ml and resistant when MIC≥16 µg/ml. When using the bacterial length (enlargement), the new breakpoint concentrations for ceftazidime were empirically correlated in similar manner as described in Example 1, except that according to the MIC-CLSI standards an additional value for intermediate resistance was not determined Those correlated breakpoint concentrations for enlargement were 0.5 µg/ml for susceptible strains and greater than 1.25 µg/ml for resistant strains. Stated differently, strains were considered to be susceptible when they demonstrated cell enlargement in response to concentrations of 0.5 µg/ml and 1.25 µg/ml and were considered to be intermediate when they demonstrated cell enlargement in response to only the 1.25 µg/ml dose. Strains were considered to be resistant when no cell enlargement was presented at either concentration. 61 strains of *K. pneumoniae* were studied, including 31 susceptible, 16 intermediate and 14 resistant to ceftazidime, according to the standard criterion of growth affectation as indicated by MIC-CLSI.

Each strain was incubated with 0.5 µg/ml and 1.25 µg/ml ceftazidime and evaluated for enlargement in the manner described in Example 2. Each of the sixty-one strains were correctly identified using the new breakpoint concentrations and assessing enlargement/non-enlargement.

Example 4

*Pseudomonas aeruginosa*, a common source of dangerous nosocomial infections, was also evaluated. According to the CLSI criteria, a strain of *Pseudomonas aeruginosa* is classified as susceptible to ceftazidime when the MIC≤8 µg/ml and resistant when MIC≥32 µg/ml. New breakpoint concentrations for ceftazidime were correlated based on cell enlargement, as described in Example 3. Those correlated breakpoint concentrations for enlargement were 0.5 µg/ml for susceptible strains and greater than 1.0 µg/ml for resistant strains.

130 strains of *P. aeruginosa* were studied, including 117 strains susceptible to ceftazidime, 8 intermediate strains and 5 strains classified as resistant to ceftazidime according to CLSI criteria. After incubation for an hour with 0.5 µg/ml ceftazidime and 1 µg/ml ceftazidime, each strain was correctly categorized based on an assessment of enlargement/non-enlargement. Susceptible strains appeared enlarged after incubation with 0.5 µg/ml and 1 µg/ml, intermediate strains only after 1 lag/ml, whereas resistant strains never appeared enlarged after both doses.

Example 5

*P. aeruginosa* was evaluated for the effect of carbapenems, meropenem and imipenem, which we corroborate that induce cell enlargement in the susceptible strains of this bacterium. CLSI breakpoint concentrations of susceptibility and resistance correspond to MICs≤2-≥8 µg/ml, respectively. For cell enlargement, the new breakpoint concentrations were much lower: ≤0.2-≥0.5 µg/ml, for susceptibility and resistance, respectively. One hundred and thirty strains of *P. aeruginosa* were studied, obtaining 97 susceptible, 14 intermediate and 19 resistant to meropenem, following the standard criterion of growth affectation as indicated by MIC-CLSI. All these strains were correctly categorized when using the new breakpoints for enlargement/non-enlargement. Susceptible strains appeared enlarged after incubation with 0.2 µg/ml and 0.5 µg/ml, intermediate strains only after 0.5 µg/ml, whereas resistant strains never appeared enlarged after both doses.

Examples 2 and 3 demonstrated that after incubating an exponentially growing culture with 2 µg/ml or 0.5 µg/ml of ceftazidime 1 hour, it is possible to distinguish if a strain of *A. baumannii* or *K. pneumoniae* respectively, is susceptible or not to the cephalosporin, by examination of cell enlargement. This is the relevant and urgent information that the clinician requires to determine antibiotic treatments, such as, whether or not to continue the use of a cephalosporin or to change antibiotics. Similarly, Examples 4 and 5 illustrate that numerous species of microorganism may be rapidly screened for their susceptibility to antibiotics once values are correlated to accepted measurements of susceptibility and resistance. Bacterial cell size or length may be applied for a rapid discrimination of the susceptibility or resistance to other antibiotics and bacterial species, once the breakpoint concentrations for cell enlargement that correlate with the standard breakpoint concentrations established for cell growth by the specific regulatory organisms, are obtained by the methodologies previously described.

Those skilled in the art will recognize that the invention described includes a number of inventive features, which may be provided in any number of combinations and includes at least the following:

As can be easily understood from the foregoing, the basic concepts of the present invention may be embodied in a variety of ways. The invention involves numerous and varied embodiments including, but not limited to, the best mode of the invention.

As such, the particular embodiments or elements of the invention disclosed by the description or shown in the figures or tables accompanying this application are not intended to be limiting, but rather examples of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

Moreover, for the purposes of the present description and claims, the term "a" or "an" entity refers to one or more of that entity; for example, "an antibiotic" refers to one or more antibiotics. As such, the terms "a" or "an", "one or more" and "at least one" should be understood as interchangeable as used herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

In addition, as to each term used it should be understood that unless its utilization in this application is inconsistent with such interpretation, common dictionary definitions should be understood to be included in the description for each term as contained in the Random House Webster's Unabridged Dictionary, Second edition, each definition hereby incorporated by reference.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method of rapidly evaluating the susceptibility of an isolated strain of a species of bacteria to a cell wall synthesis inhibiting antibiotic comprising:
   a) culturing an isolated strain of a gram-negative bacteria in a liquid broth or on an agar media, the gram-negative bacteria coming from a patient, wherein one or more minimum inhibitory concentrations of the cell wall synthesis inhibiting antibiotic have been established for the species of bacteria;
   b) preparing a dose of a cell wall synthesis inhibiting antibiotic at a concentration that i.) is lower than the corresponding minimum inhibitory concentration and ii.) results in cell enlargement or an increase in cell size in strains of the gram-negative bacteria that are susceptible to the cell wall synthesis inhibiting antibiotic but not in strains of bacteria that are resistant to the cell wall synthesis inhibiting antibiotic;
   c) combining the dose of cell wall synthesis inhibiting antibiotic prepared in step b) with the cultured bacteria;
   d) incubating the combined cultured bacteria and the dose of cell wall synthesis inhibiting antibiotic; and
   e) detecting cell enlargement or an increase in cell size in the strain of the gram-negative bacteria and classifying the susceptibility of the gram negative bacteria to the cell wall synthesis inhibiting antibiotic.

2. The method as claimed in claim 1, wherein the step of culturing an isolated strain of gram-negative bacteria further comprises establishing an exponentially growing bacteria culture.

3. The method as claimed in claim 1, further comprising more than one dose, wherein the concentrations of the more than one dose of cell wall synthesis inhibiting antibiotic are correlated to the minimum inhibitory concentrations for susceptible, intermediate, or resistant classifications of the gram-negative bacteria.

4. The method as claimed in claim 1, further comprising the step of immobilizing a sample of the incubated bacteria on a slide prior to step e).

5. The method as claimed in claim 1, wherein the step of detecting cell enlargement or an increase in cell size is performed by bright field microscopy, dark field microscopy, fluorescence microscopy, phase contrast microscopy, or polarized light microscopy.

6. The method as claimed in claim 1, wherein the step of detecting cell enlargement or an increase in cell size further comprises diffusion across a filter.

7. The method as claimed in claim 1, wherein the step of detecting cell enlargement or an increase in cell size further comprises staining the gram-negative bacteria being assessed.

8. The method as claimed in claim 1, wherein the step of detecting cell enlargement or an increase in cell size is performed by flow cytometry.

9. The method as claimed in claim 1, wherein steps b) to e) of claim 1 are performed within two hours, within an hour and a half, or within one hour.

10. The method as claimed in claim 1, wherein the step of culturing an isolated strain of a gram-negative bacteria further comprises isolating bacteria responsible for producing an infectious disease in the patient.

11. The method as claimed in claim 1, wherein the cell wall synthesis inhibiting antibiotic comprises an antibiotic which inhibits peptidoglycan synthesis.

12. The method as claimed in claim 1, wherein the cell wall synthesis inhibiting antibiotic comprises an antibiotic from the β-lactams family or a glycopeptide.

13. The method as claimed in claim 1, wherein the cell wall synthesis inhibiting antibiotic comprises a cephalosporin or carbapenem.

14. The method as claimed in claim 1, wherein the gram-negative bacteria comprises a gram-negative bacilli.

15. The method as claimed in claim 1 further comprising the step of:
    classifying the strain of the gram-negative bacteria as either susceptible, intermediate or resistant based on the presence or absence of cell enlargement or an increase in cell size in response to the at least two doses.

\* \* \* \* \*